United States Patent
Kaiser et al.

(10) Patent No.: US 10,335,097 B2
(45) Date of Patent: Jul. 2, 2019

(54) PATIENT-SUPPORTING UNIT FOR A DEVICE FOR SUPPORTING A PATIENT, WHO IS TO BE X-RAYED, DURING AN OPERATION

(71) Applicant: MAQUET GMBH, Rastatt (DE)

(72) Inventors: Jochen Kaiser, Karlsruhe (DE); Ulrich Wyslucha, Weingarten (DE); Stefan Peter, Rastatt (DE); Siegfried Hund, Oberkirch (DE)

(73) Assignee: MAQUET GMBH, Rastatt (DE)

( * ) Notice: Subject to any disclaimer, the term of this patent is extended or adjusted under 35 U.S.C. 154(b) by 616 days.

(21) Appl. No.: 15/096,307

(22) Filed: Apr. 12, 2016

(65) Prior Publication Data

US 2016/0235376 A1 Aug. 18, 2016

Related U.S. Application Data

(63) Continuation-in-part of application No. PCT/EP2014/072324, filed on Oct. 17, 2014.

(30) Foreign Application Priority Data

Oct. 18, 2013 (DE) ........................ 10 2013 111 519

(51) Int. Cl.
*A61B 6/04* (2006.01)
*A61G 13/12* (2006.01)
*A61G 13/10* (2006.01)

(52) U.S. Cl.
CPC ............ *A61B 6/0407* (2013.01); *A61G 13/12* (2013.01); *A61G 13/122* (2013.01);
(Continued)

(58) Field of Classification Search
CPC .... A61B 6/0407; A61G 13/12; A61G 13/101; B60N 2/809; B60N 2/818
See application file for complete search history.

(56) References Cited

U.S. PATENT DOCUMENTS

| 5,088,706 A | 2/1992 | Jackson |
| 5,147,287 A | 9/1992 | Jewell et al. |

(Continued)

FOREIGN PATENT DOCUMENTS

| CN | 202342383 U | 7/2012 |
| DE | 102006059733 A1 | 6/2008 |

(Continued)

OTHER PUBLICATIONS

International Search Report dated Feb. 24, 2015 issued for corresponding international application No. PCT/EP2014/072324, 3 pages, with translation (2 pages).

(Continued)

*Primary Examiner* — Eric J Kurilla
(74) *Attorney, Agent, or Firm* — Aaron M. Miller

(57) ABSTRACT

A patient-supporting device is disclosed. The patient-supporting device includes a fastening assembly that fastens the patient-supporting device to a structural member, a support member configured to receive a body part of a patient, and a height adjustment assembly that adjusts a distance between the fastening assembly and the support member. The height adjustment assembly includes a locking assembly and an elongated member. The support member is attached to a first end portion of the elongated member. The locking assembly is stationary relative to the fastening assembly. The elongated member is guided in an aperture of the locking assembly in a longitudinal direction of the elongated member. A plurality of first snap-in recesses is disposed on a first side portion of the elongated member. The locking assembly includes a first locking member.

21 Claims, 9 Drawing Sheets

(52) U.S. Cl.
CPC ....... *A61G 13/123* (2013.01); *A61G 13/1225* (2013.01); *A61G 13/101* (2013.01); *A61G 2210/50* (2013.01)

(56) References Cited

U.S. PATENT DOCUMENTS

| | | | |
|---|---|---|---|
| 5,806,117 | A | 9/1998 | Gotfried |
| 6,076,525 | A | 6/2000 | Hoffman |
| 6,154,901 | A | 12/2000 | Carr |
| 6,394,553 | B1 | 5/2002 | McAllister et al. |
| 7,520,007 | B2 | 4/2009 | Skripps |
| 7,600,281 | B2 | 10/2009 | Skripps |
| 2005/0081865 | A1 | 4/2005 | Hubert et al. |
| 2005/0082893 | A1* | 4/2005 | Akehi ................... B60N 2/818 297/410 |
| 2005/0200185 | A1* | 9/2005 | Yokoyama ............ B60N 2/818 297/410 |
| 2005/0280305 | A1* | 12/2005 | Gurtatowski ......... B60N 2/818 297/410 |
| 2006/0163931 | A1* | 7/2006 | Yamada ................ B60N 2/818 297/410 |
| 2006/0214492 | A1* | 9/2006 | Hassler ................. B60N 2/818 297/410 |
| 2006/0248650 | A1 | 11/2006 | Skripps |
| 2006/0255220 | A1 | 11/2006 | Skripps |
| 2006/0284468 | A1* | 12/2006 | Tanaka .................. B60N 2/818 297/410 |
| 2013/0269710 | A1 | 10/2013 | Hight et al. |
| 2016/0213543 | A1* | 7/2016 | Hafner ................ A61G 13/101 |

FOREIGN PATENT DOCUMENTS

| | | |
|---|---|---|
| DE | 102009004554 A1 | 7/2009 |
| DE | 202013100213 U1 | 3/2013 |
| EP | 1785123 A2 | 5/2007 |
| EP | 2325502 A1 | 5/2011 |
| EP | 1874256 A4 | 9/2012 |
| EP | 1874256 B1 | 11/2013 |
| JP | 2002-034710 A | 2/2002 |
| JP | 2004-513748 A | 5/2004 |
| RU | 2161942 C1 | 1/2001 |
| WO | 2009/029524 A1 | 3/2009 |
| WO | 2013/069952 A1 | 5/2013 |
| WO | 2014/057344 A2 | 4/2014 |

OTHER PUBLICATIONS

Russian Office Action and Russian Search Report (with English translations) dated Mar. 28, 2018 which issued during the prosecution of corresponding Russian Patent Application No. 2016118962, 12 pages.

Japanese Office Action (including English translation) dated Oct. 16, 2018 for corresponding Japanese Patent Application No. 2016-523330, 6 pages.

Chinese Office Action and Chinese Search Report (Chinese and English translations) dated Mar. 21, 2017 which issued during the prosecution of corresponding Chinese Patent Application No. 201480064251.4, 19 pages.

\* cited by examiner

PATIENT-SUPPORTING UNIT FOR A DEVICE FOR SUPPORTING A PATIENT, WHO IS TO BE X-RAYED, DURING AN OPERATION

CROSS REFERENCE TO RELATED APPLICATIONS

The present application is a continuation-in-part filed under 35 U.S.C. § 111(a), and claims the benefit under 35 U.S.C. §§ 365(c) and 371 of PCT International Application No. PCT/EP2014/072324, filed Oct. 17, 2014, and which designates the United States of America, and German Patent Application No. 10 2013 111 519.5, filed Oct. 18, 2013. The disclosures of these applications are herein incorporated by reference in their entirety.

TECHNICAL FIELD

The present disclosure relates to a patient-supporting unit for a device on which a body part of a patient, who is to be x-rayed, can rest during an operation. The patient-supporting unit may comprise a fastening unit for fastening the patient-supporting unit to a rail of the device, and a resting pad on which the patient can rest.

BACKGROUND

In various operations, for example in back surgery, a patient is x-rayed during the operation. For this purpose, C-shaped x-ray apparatuses are commonly used, wherein the patient is supported in the opening of the "C." In particular, C-arcs that can be swiveled by up to 270° are also used for recording 3D images. The use of conventional operating tables in these applications may be limited because x-raying may occur in a limited range. For recording 3D-views, the C-arc may be moved relatively closely to the patient over a relatively large area. The standard patient rests of operating tables may be too wide for this purpose. Additionally, operating tables frequently include relatively thick, metal-containing constructions, so that x-raying may occur with insufficient quality. Another factor may be that the thicknesses and the contours of constructions of operating room equipment (e.g., operating tables) may be different, which may result in unsuitable x-ray images and may limit x-ray recording using the C-arc.

Therefore, devices for supporting the patient that can be attached to the operating table may be used. The patient's torso, which is to undergo the surgery and is to be x-rayed, then rests on the attached device, while the legs of the patient rest on the operating table itself.

Such a device for supporting a patient during surgery is known, for example, from the document U.S. Pat. No. 7,600,281 B2. The device described therein comprises two bars extending parallel to one another, the bars being fastened on one side to the operating table and on the other side to a stand. On the bars, several resting surfaces are provided, on which the patient (e.g., the torso and hips of the patient) can be supported. Here, the resting surfaces protrude over the entire area between the two bars, connecting them to one another.

The above-described device has the disadvantage that, due to the resting elements, the quality of a recorded x-ray image may be unsuitable. The contours of the resting elements may appear in the x-ray image, which can lead to misinterpretation. In addition, the rigid resting elements may provide for insufficient adaptation to the individual anatomy of the patient, so that the patient may not be suitably supported for the operation.

SUMMARY OF THE DISCLOSURE

A patient-supporting unit for a device for supporting a patient, who is to be x-rayed, during an operation is disclosed. The patient-supporting unit may enable an optimal secure supporting of the patient.

The patient-supporting unit may comprise a fastening unit for fastening the patient-supporting unit to a rail of the device for supporting the patient, and a resting pad on which a body part of the patient can rest. Furthermore, a height adjustment unit may be provided for varying the distance between the fastening unit and the resting pad within a predetermined setting range. For example, a height of the resting pad on which a partial area of the body of the patient rests can be set relative to the fastening unit and thus relative to the rail on which the patient-supporting unit is supported. For example, the supporting of the patient can be adapted optimally to the individual anatomical circumstances of the patient and the respective operations to be performed.

For example, it may be possible to dispense with stacks of cushions for raising individual areas of the body. Based on the height adjustment of the resting pad using the height adjustment unit, the resting pad may be firmly connected to the rail, so that this pad (e.g., in contrast to a stack of cushions) may not slip. In addition, the use of such a resting pad (e.g., in contrast to cushions) may not result in varying the permeability to x-rays. When several cushions are stacked, the permeability to x-rays may become less suitable (e.g., as the number of cushions that are used increases) so that x-ray images of unsuitable quality are recorded. In addition, stacking several cushions one on top of the other may result in the cushions slipping with respect to one another, and thus the supporting of the patient no longer being suitable.

The resting pad may comprise a fixed supporting structure and a cushion attached to said supporting structure, so that the patient is comfortably supported.

For example, the patient-supporting unit may be configured so that it can be attached to rails of a device for supporting a patient to be x-rayed. In order to be able to x-ray a patient, for example during back surgery, the patient may not be supported on the operating table itself, but on a device that may be attached to said operating table. Such a device may comprise two rails extending parallel to one another, of which in each case one end may be fastened to the operating table (e.g., to the welding sites of the operating table for leg sections) and the other ends may be attached to another stand. On these rails, a plurality of these patient-supporting units may be attached, by which the different areas of the patients of the body of the patient may be supported. The individual patient-supporting units may be individually slidable on the rails, and for example (e.g., in combination with the height adjustment) may be individually adaptable to the anatomy of the patient in a relatively simple manner. For example, during back surgery, two such patient-supporting units may be used for supporting the torso, and another two patient-supporting units may be used for supporting the hips of the patient. In this case, the legs of the patient may rest, for example, on the central portion and/or the back section of the operating table itself.

The predetermined setting range may include, for example, the range within which the distance between the resting pad and the fastening unit and thus the distance between the resting pad and the rail can be varied.

The height adjustment unit may be configured, for example, so that the distance between the fastening unit and the resting pad can be adjusted by at least 5 cm (for example, between about 5 cm and about 10 cm, or at least 8 cm). This may provide for a sufficiently large adjustment possibility for different operations and different anatomies of the patients.

For example, the distance can be set stepwise within the setting range. For example, five evenly distributed steps may be provided (e.g., so that a sufficiently small-step adjustment possibility exists). Alternatively, the adjustment can also occur continuously.

For example, the height adjustment unit may comprise a locking unit and a rod, wherein the resting pad may be fastened to a first end of the rod. The locking unit may be stationarily arranged relative to the fastening unit and, for example, may form a single part with this fastening unit. The rod may be slidably guided in a receptacle of the locking unit in a longitudinal direction of the rod, so that, via this slidable guiding, the distance between the resting pad firmly connected to the rod and the fastening unit may be adjustable relative to one another.

On a first side or first side portion of the rod, a plurality of snap-in recesses may be provided. The snap-in recesses may be used for snapping-in a first locking bar of the locking unit. When the first locking bar is arranged in a locked position, then it may engage in one of the snap-in recesses, so that, depending on which snap-in recess it engages in, there may be a different distance between the resting pad and the fastening unit. The distance can be varied by moving the rod either further into the recess or through the recess. When the first locking bar engages in one of the snap-in recesses, it may substantially prevent at least a movement of the rod in a first direction (e.g., wherein during the fastening of the patient-supporting unit to a horizontally oriented rail, this first direction may be directed vertically downward). Thus, via the first locking bar, the rod and/or the resting pad may be prevented from being moved downward when this first locking bar is arranged in the locked position. As a result, for example, suitable (e.g., secure) support of the patient may be provided.

For example, the first snap-in recesses, viewed in the first direction, may have a beveled configuration so that the rod is movable, in a second direction opposite the first direction (e.g., in an upward direction, for example also when the first locking bar is arranged in the locked position). Due to the beveled configuration in the first direction, the locking bar may be moved automatically out of the locked position during a movement of the rod in the second direction (e.g., towards the beveled edge, so that the rod can be moved for example in the second direction). Also for example, viewed in the second direction, the recess may not be beveled, so that a movement in the first direction of the rod may be reduced and/or substantially suppressed. For example, the first locking bar may also be beveled so that it promotes a movement (e.g., automatic movement) of the first locking bar out of the locked position.

Also for example, the first locking bar may be movable between the locked position and an unlocked position, wherein, in the unlocked position, the first locking bar may not reduce or substantially prevent a movement of the rod in the first direction. The first locking bar may be swivelably mounted for example about a rotation axis, and may be rotated between the locked position and the unlocked position about this rotation axis.

Further for example, the first locking bar may be preloaded by a resilient element (e.g. in the locked position) and a first lever may be provided for the movement of the first locking bar against the resetting force of the resilient element (e.g., from the locked position into the unlocked position). Accordingly, the locking bar may automatically be engaged in the snap-in recesses (and for example may not be inadvertently forgotten by a user). The resilient element may comprise a flexion spring (e.g., a plastic flexion spring), for example so that a suitable (e.g., secure) holding of the locking bar in the locked position is provided.

Also for example, on a second side or second side portion of the rod, a plurality of second snap-in recesses may be provided. For example, the locking unit may comprise a second locking bar, wherein for example, in a locked position, the second locking bar may engage in one of the second snap-in recesses and thus reduce and/or substantially prevent a movement of the rod in the first direction. Thus, the locking of the rod via two locking mechanisms operating separately from one another may occur, so that a suitable (e.g., secure) holding of the resting pad in the desired position may be facilitated (e.g., implemented) and a sinking (e.g., an inadvertent sinking) of the resting pad may be reduced and/or substantially prevented. For example, the use of the two separate locking mechanisms may substantially prevent a release (e.g., an inadvertent release) of the lock and thus a downward sinking (e.g., an inadvertent downward movement or sinking) of the patient. Each one of the locking mechanisms may be designed so that it suitably (e.g., reliably) holds the admissible resting weight of the patient-supporting unit. Thus, the first locking mechanism and the second locking mechanism may be provided (e.g., implemented) redundantly.

The first and the second snap-in recesses may be arranged, for example, on opposite portions or sides of the rod. For example, the first locking mechanism may be constructed via the first locking bar and the first snap-in recess, and the second locking mechanism may be constructed via the second locking bar and the second snap-in recess.

The second snap-in recesses, for example as viewed in the first direction, may also be beveled so that the rod is movable in the second direction, e.g., when the second locking bar is arranged in the locked position. For example, the rod and the resting pad may be pulled upward in order to increase the distance from the fastening unit (e.g., without actuating the lever and moving the locking bars into the unlocked position to achieve this purpose). The snap-in recesses and the locking bars for example operate similarly to a free wheel (e.g., against the first movement direction). Also for example, the second locking bar may be beveled so that it provides for an automatic movement of the second locking bar out of the locked position. Also for example, via the two locking bars (e.g., alone), a movement of the rod in the first direction (for example, downward) may be substantially prevented. For example, both locking mechanisms may be designed so that both the first locking bar and also the second locking bar are capable of sustaining a desired weight (e.g., an admissible weight or a maximum admissible weight) resting on the resting pad. For example, if one of the locking bars is arranged in the locked position, a movement of the rod in the first direction is still reduced or substantially prevented.

The second locking bar may also be movable (e.g., swivelably movable) between a locked position and an unlocked position wherein for example, in the unlocked position, the second locking bar may provide for (e.g., enable) a movement of the rod in the first direction.

Also for example, the second locking bar may be preloaded by a resilient element (e.g., a flexion spring or a plastic flexion spring) in the locked position, and a second lever may be provided for moving the second locking bar against the resetting force of the resilient element (e.g., from the locked position to the unlocked position).

Also for example, for the unlocking (e.g., the movement of the first locking bar or of the second locking bar from the locked position into the unlocked position) the first lever and the second lever may be actuated in opposite directions. For example, the two levers may be moved toward one another. For example, a simple actuation with one hand may be performed (for example, one lever may be gripped with a thumb and the other lever may be gripped with the index finger on the outer side thereof and the levers may be moved towards one another). Also for example, by a movement in the opposite direction, an unintended actuation (e.g., brushing by a user) may be substantially prevented.

The ends of the levers which are actuated by the operating person of the patient-supporting unit (e.g., the ends facing away from the locking bars) may be arranged, for example, within a recess of a housing. For example, the possibility of inadvertent actuation of the levers and thus an unsuitable release of the locking of the height adjustment unit may be substantially prevented.

For example, the rod may be movable in the first direction if both the first locking bar and also the second locking bar are disposed (e.g., arranged) in the unlocked position. For example, the two locking bars may be configured so that they can support or sustain a desired weight (e.g., the maximum admissible weight) for the patient-supporting unit by themselves. For example, double locking may be achieved, and an unsuitable release (e.g., unintentional release) may be prevented.

For example, the rod may have a groove into which a pin connected (e.g., firmly connected) to the fastening unit protrudes. The pin may be guided within the groove. A twisting of the rod relative to the fastening unit may be reduced or substantially prevented by the groove. A twisting of the resting pad connected (e.g., firmly connected) to the rod may also be reduced or substantially prevented by the groove. Also for example, via the groove, the setting range (e.g., within which the height adjustment thereof may be facilitated or provided) may be limited. For example, the likelihood that the fingers of an operating person may become unsuitably disposed between the resting pad and the fastening unit may be substantially prevented (e.g., because the groove may be configured so that a sufficiently large minimum distance between the upper side of the fastening unit and the lower side of the resting pad is present).

A resilient abutment may be provided at at least one end of the groove. The abutment may be used to establish a tolerance compensation that may, for example, damp movement at the end of the groove.

Also for example, the resting pad, the height adjustment unit and/or the fastening unit may be constructed without metal. For example, the resting pad, the height adjustment unit and/or the fastening unit may be constructed from a material that is sufficiently permeable to x-rays so that a suitable x-ray image is recorded (such as, for example, from a carbon-fiber-reinforced plastic). For example, an x-ray image or a 3D x-ray view can be recorded in the area of the resting pads, and the resting pads may not be visible consistently in the x-ray image or alternatively may be visible to a satisfactorily low degree in at least one area of the surface. Thus, unsuitable interpretations of the x-ray image may be prevented.

The fastening unit may comprise, for example, a U-shaped receptacle, which, for example during the mounting of the patient-supporting unit may be disposed (e.g., stuck) on the corresponding rail from above (e.g., so that the rail may be received within the U-shaped receptacle). On one arm of the U-shaped receptacle, a closing plate may be swivelably disposed or arranged, which for example can be attached by a screw to the other arm (e.g., resulting in a closed rectangular cross section within which the rail may be received). For example, a quick attachment of the patient-supporting units to the rails may be achieved. Also for example, this attachment may be released and reestablished in a relatively simply manner. The screw may be tightened and loosened, for example, manually without a tool.

In at least some exemplary embodiments (e.g., in addition to the height adjustment unit), a cross adjustment unit may also be provided, by which the resting pad may be movable relative to the height adjustment unit in a predetermined cross adjustment range. The cross adjustment unit may comprise, for example, a rail arranged on the resting pad, in which the first end of the rod engages. For this purpose, the end may be for example configured to be complementary to the rail shape.

As a result of the cross adjustment, the spacing of resting pads of two patient-supporting units arranged adjacently to one another on adjacent rails extending parallel to one another can be adjusted so that the free space between the resting pads can optionally be increased (e.g., in order to generate thereby a larger x-ray range). Conversely for example, the spacing can be decreased if this is appropriate for the supporting of the patient.

The adjustment directions of the height adjustment unit and the cross adjustment unit (e.g., the two directions in which the resting pad can be adjusted by the respective adjustment unit) may be oriented, for example, orthogonally with respect to one another. The resting pad may be slidable relative to the rod, e.g. in a third direction oriented orthogonally to the first and to the second direction.

In at least some exemplary embodiments, the first, the second and also the third direction may be oriented orthogonally to the respective direction in which the patient-supporting unit can be shifted on the rail, so that, for example, the patient-supporting unit can be adjusted in three directions that are orthogonal to one another (e.g., three directions that are all orthogonal to each other). This may result, for example, in suitable individual adaptability to the individual circumstances of a patient, which may provide suitable support.

BRIEF DESCRIPTION OF THE DRAWINGS

Additional features of the present disclosure are described below, with reference to the appended figures.

DETAILED DESCRIPTION AND INDUSTRIAL APPLICABILITY

Figure 1:
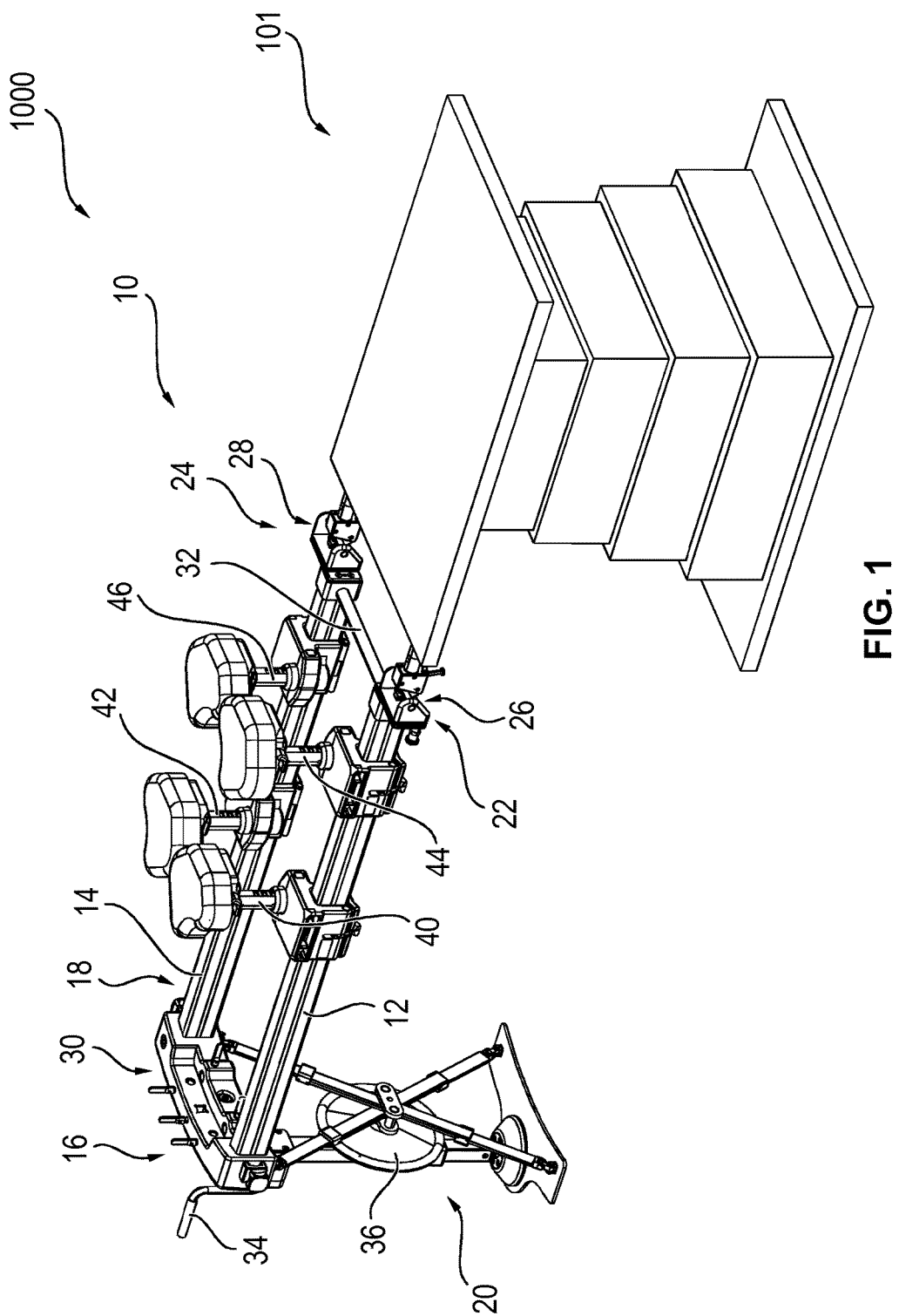
FIG. 1 shows a diagrammatic perspective representation of an exemplary arrangement for supporting a patient, who is to be x-rayed, during an operation.
Figures 2, 3:
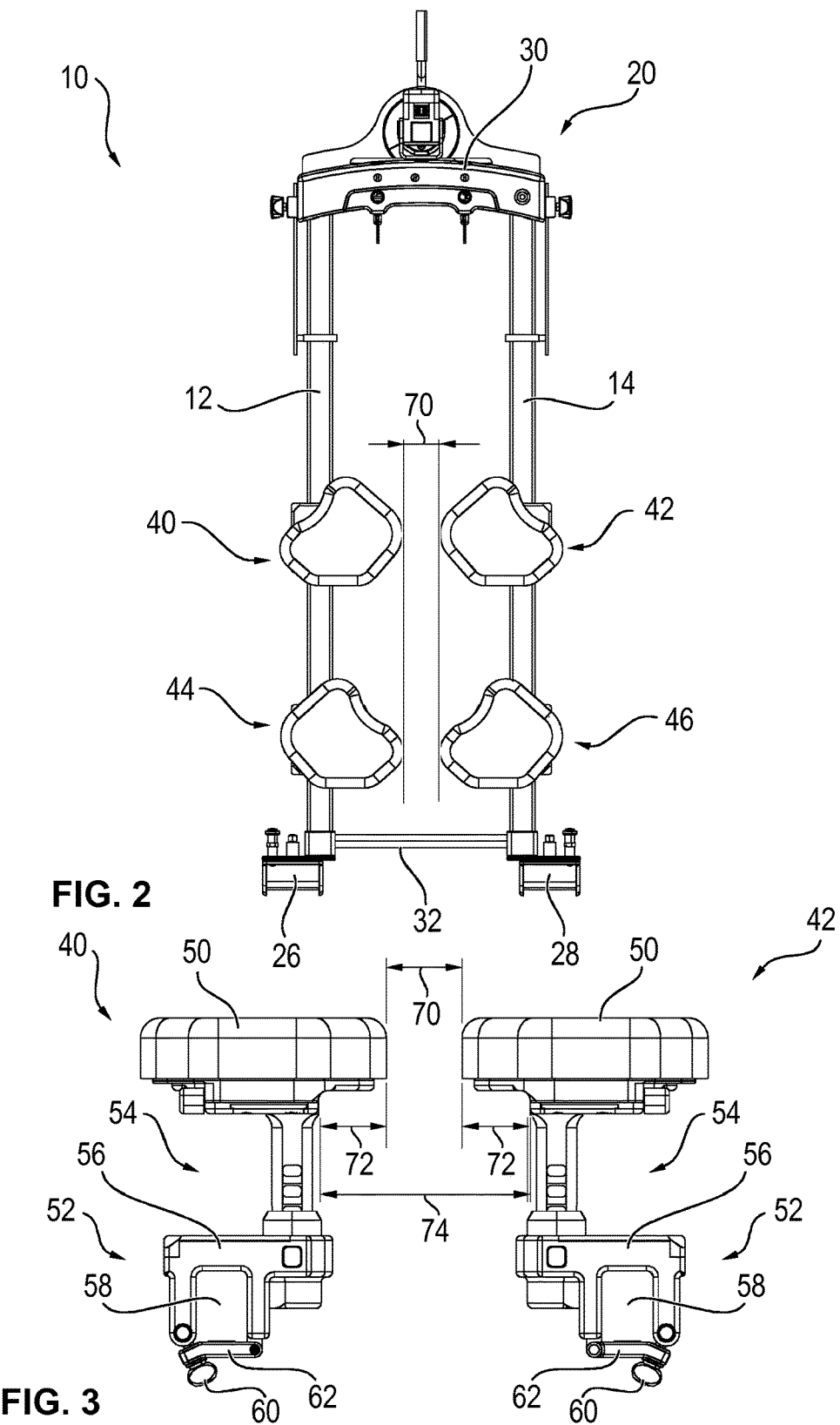
FIG. 2 shows a top view on an exemplary device of the arrangement according to FIG. 1.
FIG. 3 shows a side view of two exemplary patient-supporting units of the device according to FIG. 2.

In FIG. 1, a diagrammatic perspective representation of an arrangement 1000 for supporting a patient during an operation is illustrated. The arrangement may comprise an operating table 101 and a device 10 for supporting the area of the body of the patient that is to be x-rayed. FIG. 2 shows a top view on this device 10 according to FIG. 1.

In at least some exemplary embodiments, the device 10 may be used to support a patient during back surgery. In such back surgeries, such as for example spinal surgeries, the patients may be x-rayed during the operation, for which purpose a C-shaped x-ray apparatus may be used. For example, the C-arc of the x-ray apparatus may be moved around the patient for recording 3D images. As described further below, the device 10 may be configured so that it can be used to generate a suitable (e.g., a qualitatively high-value) x-ray image in a relatively simple manner. A patient may not be supported on an operating table, because such an operating table may not allow for x-raying with suitable quality and in suitable areas. For example, the large (e.g., massive) foot column of an operating table may limit the possible x-raying length, and an operating table may include an unsuitable amount of metal-containing construction elements that are unsuitable for producing an x-ray image. In addition, the patient-supporting surface of an operating table may be too wide for suitable recording of 3D views by the C-arc used.

The device 10 may comprise two structural members such as, for example, rails 12, 14, the first ends 16, 18 of which may be mounted on a stand 20. The second ends 22, 24 of the rails 12, 14, which may be opposite from the first ends 16, 18, can be fastened via fastening units 26, 28 to the operating table 101, for example, to interfaces for connecting the operating table 101 to leg sections.

The stand 20 may be used, for example, for supporting the rails 12, 14 on the floor and for providing a predetermined distance between the rails 12, 14. For example, the stand 20 may comprise a connection unit 30 by which the two first ends 16, 18 of the rails 12, 14 may be connected to one another.

Also for example, the second ends 22, 24 of the rails 12, 14 may be connected to one another via another connection unit 32, so that a desired distance between the rails 12, 14 may be maintained. The rails 12, 14 may extend parallel to one another.

The stand 20 may be configured so that it is height-adjustable, e.g., so that the distance of the rails 12, 14 from the floor can be varied. For this purpose, the stand 20 may comprise, for example, a hand crank 34 by which the height can be varied and a hand wheel 36 for fixing and stiffening the foot of the stand 20.

The operating table 101 to which the rails 12, 14 may be fastened via the fastening units 26, 28 may be height-adjustable by an actuator, so that the rails 12, 14 can be arranged horizontally at a suitable height, by setting the stand 20 and the operating table 101 appropriately.

In at least some exemplary embodiments, two patient-supporting devices or patient-supporting units 40 to 46 for supporting the patient may be arranged on the rails 12, 14. In FIG. 3 for example, two of these patient-supporting units 40, 42 are represented in a side view, wherein, for the simplification of the representation, the rails 12, 14 are not represented.

The patient-supporting units 40 to 46 may each comprise a support member such as, for example, a resting pad 50 on which the patient rests. Furthermore, the patient-supporting units 40 to 46 may each have a fastening unit 52 (e.g., a fastening assembly) for fastening the respective patient-supporting unit 40 to 46 to the respective rail 12, 14 and a height adjustment assembly such as, for example, a height adjustment unit 54 by which the resting pad 50 may be connected to the fastening unit 52 and by which the distance between the resting pad 50 and the fastening unit 52 can be set.

The fastening unit 52 may comprise a U-shaped base body 56 in the recess 58 of which the respective rail 12, 14 can be received. On the open end of the U-shaped base body, a plate 62 that is lockable via a screw 60 may be provided. For the mounting of the patient-supporting unit 40 to 46, the fastening unit 52 may be put on the respective rail 12, 14 with the plate 62 open, so that this rail may be received in the U-shaped recess 58. Subsequently, the locking bar 62 may be closed and secured via the screw 60, so that a secure and relatively simple and rapid fastening of the patient-supporting unit 40 to 46 to the rails 12, 14 may be possible. For this purpose, the screw 60 can be tightened and loosened without a tool.

The patient-supporting units 40, 42 may be used for example for supporting a patient's torso, while the patient-supporting units 44, 46 may be used for supporting the patient's hip. Thus, the patient's head may lie in a direction of the stand 20, while the patient's legs may rest on a portion of the patient-supporting surface of the operating table 101. For supporting the head, for example, additional patient-supporting units may also be fastened to the rails 12, 14.

The patient-supporting units 40, 44 may be fastened (e.g., exclusively fastened) to the first rail 12, and the patient-supporting units 42, 46 may be fastened (e.g., exclusively fastened) to the second rail 14. For example, there may be no connection between the patient-supporting units 40 and 42, as well as 44 and 46, which may be arranged next to one another.

The patient-supporting units 40 to 46 may be individually slidable independently of one another on the rails 12, 14, so that, together with the height adjustment of the patient-supporting units 40 to 46, a suitable adaptation to the individual anatomy of a patient to be operated on is provided. Therefore, in at least some exemplary embodiments, the patient-supporting units 40 to 46 may not be arranged next (e.g., directly next) to one another. For example, the resting pads 50 can be arranged at different heights. Furthermore, the distance between the resting pads 50 of adjacent patient-supporting units 40 and 42 as well as 44 and 46 can be varied. For example, the resting pads 50 may be slidably mounted transversely on the height adjustment unit 54.

Figure 4:
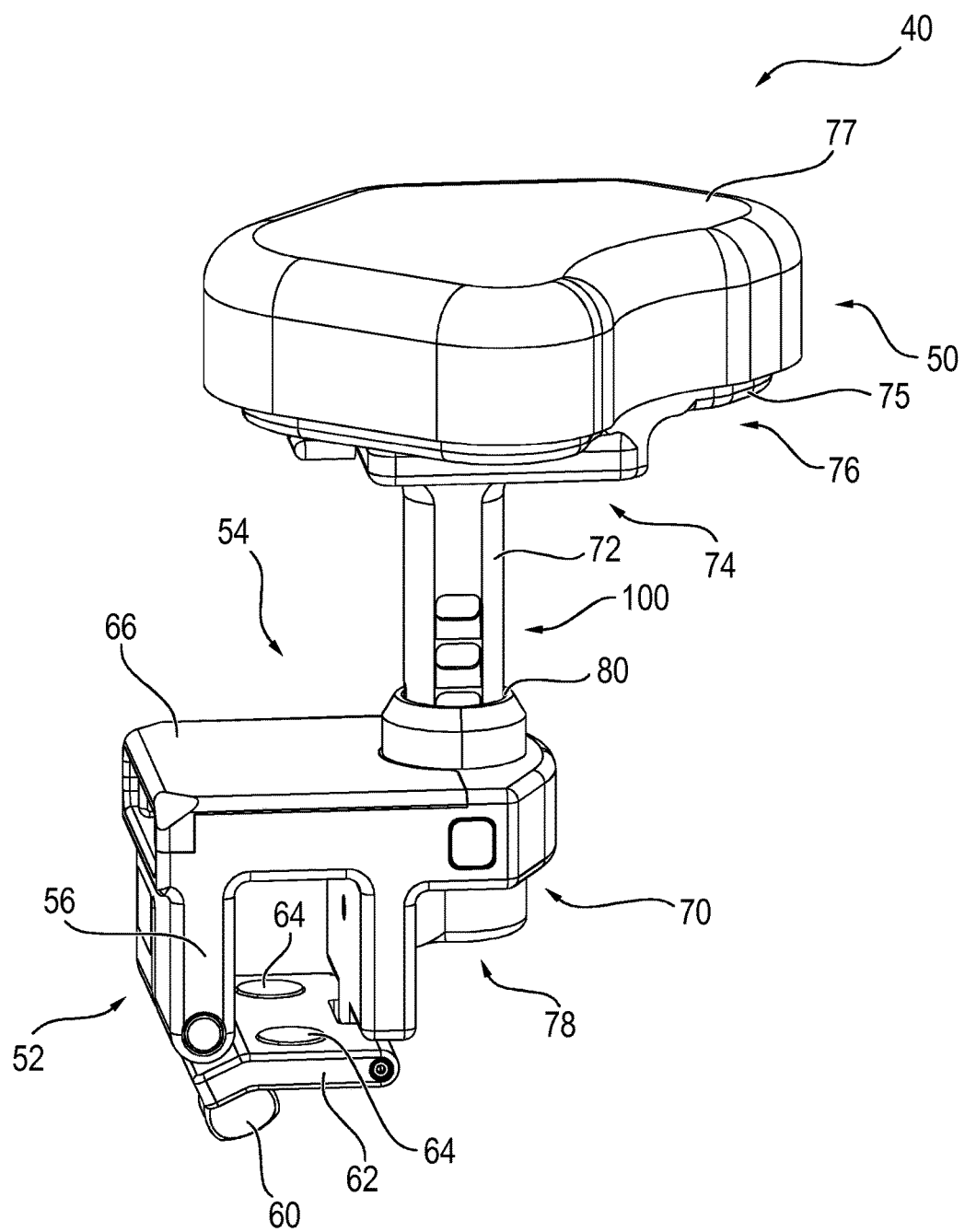
FIG. 4 shows a diagrammatic perspective representation of one of the exemplary patient-supporting units according to FIG. 3.

In FIG. 4, a diagrammatic perspective representation of the patient-supporting unit 40 is shown. The other patient-supporting units 42 to 46 may be, for example, constructed similarly (e.g., so that the following description may apply to these patient-supporting units).

On the inner side of the plate 62, two anti-slip pads 64 may be attached, which may have a high coefficient of friction and thus may substantially prevent a slipping of the fastened patient-supporting unit 40 in a longitudinal direction of the rail 12. In at least some exemplary embodiments, the anti-slip pads 64 may be made of silicone.

The height-adjustment unit 54 may comprise a locking assembly such as, for example, a locking unit 70 integrated in the housing 66 of the fastening unit 52 as well as an elongated member such as, for example, a rod 72. To the first end portion or first end 74 of rod 72, the resting pad 50 may be fastened via a cross adjustment unit 76. For example, the resting pad 50 may be attached (e.g., fastened) to the first end (74) of the rod (72). The second end 78 of the rod 72, opposite from the first end, may be guided in an aperture (e.g., receptacle or recess 80) of the locking unit 70. For example, the locking assembly (e.g., locking unit 70) may be stationary relative to the fastening assembly (e.g., fastening unit 52). Also, for example, the elongated member (e.g., rod 72) may be slidingly guided in a recess 80 of the locking assembly (e.g., locking unit 70) in a longitudinal direction of the elongated member (e.g., rod 72).

The resting pad 50 may comprise a supporting structure 75 which, for example, may be configured to be relatively stiff, and a resilient cushion 77 which may allow a comfortable supporting of the patient.

Figure 5:
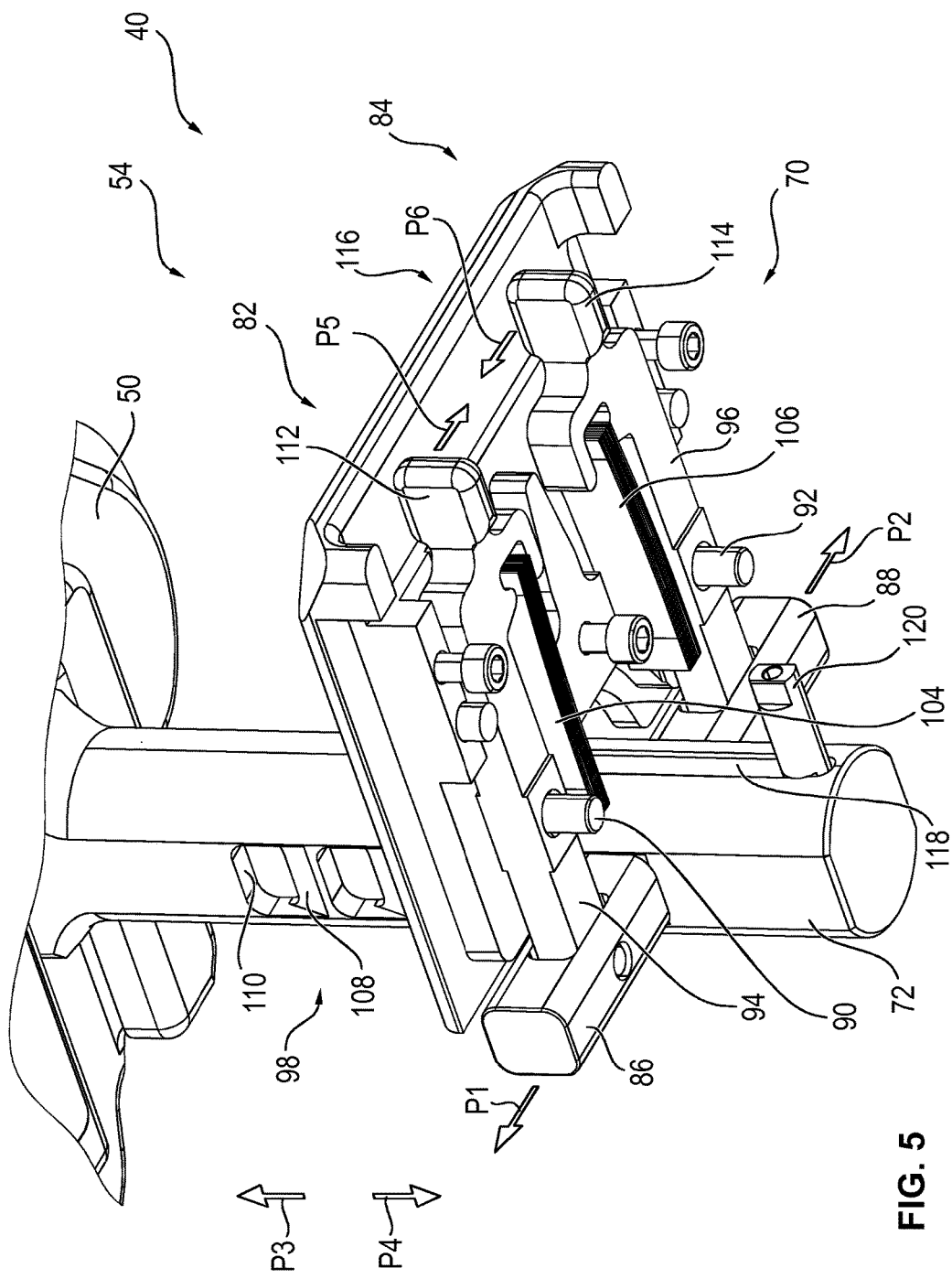
FIG. 5 shows a detail of the exemplary patient-supporting unit according to FIG. 4.
Figure 6:
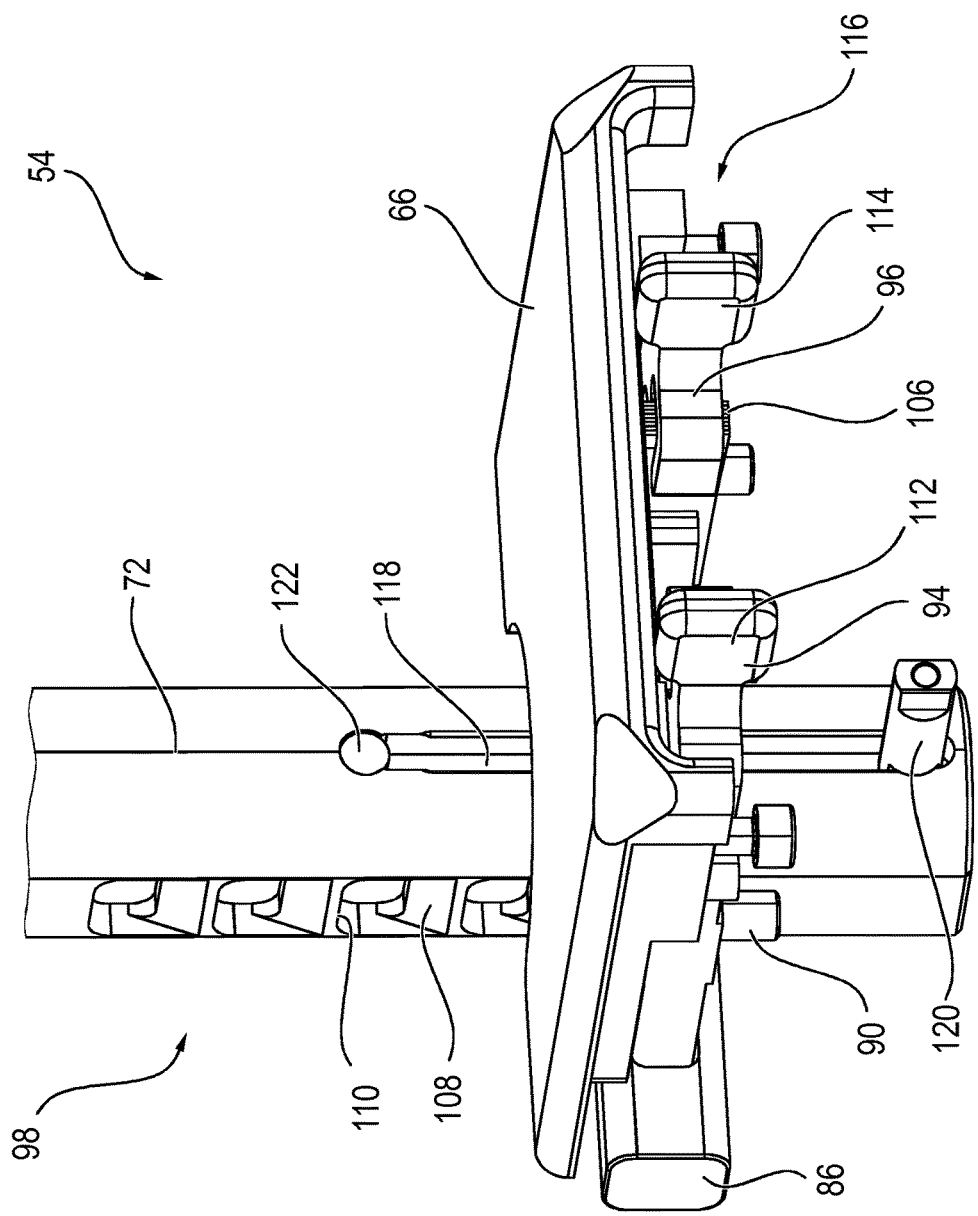
FIG. 6 shows another detail of the exemplary patient-supporting unit according to FIG. 4.
Figure 7:
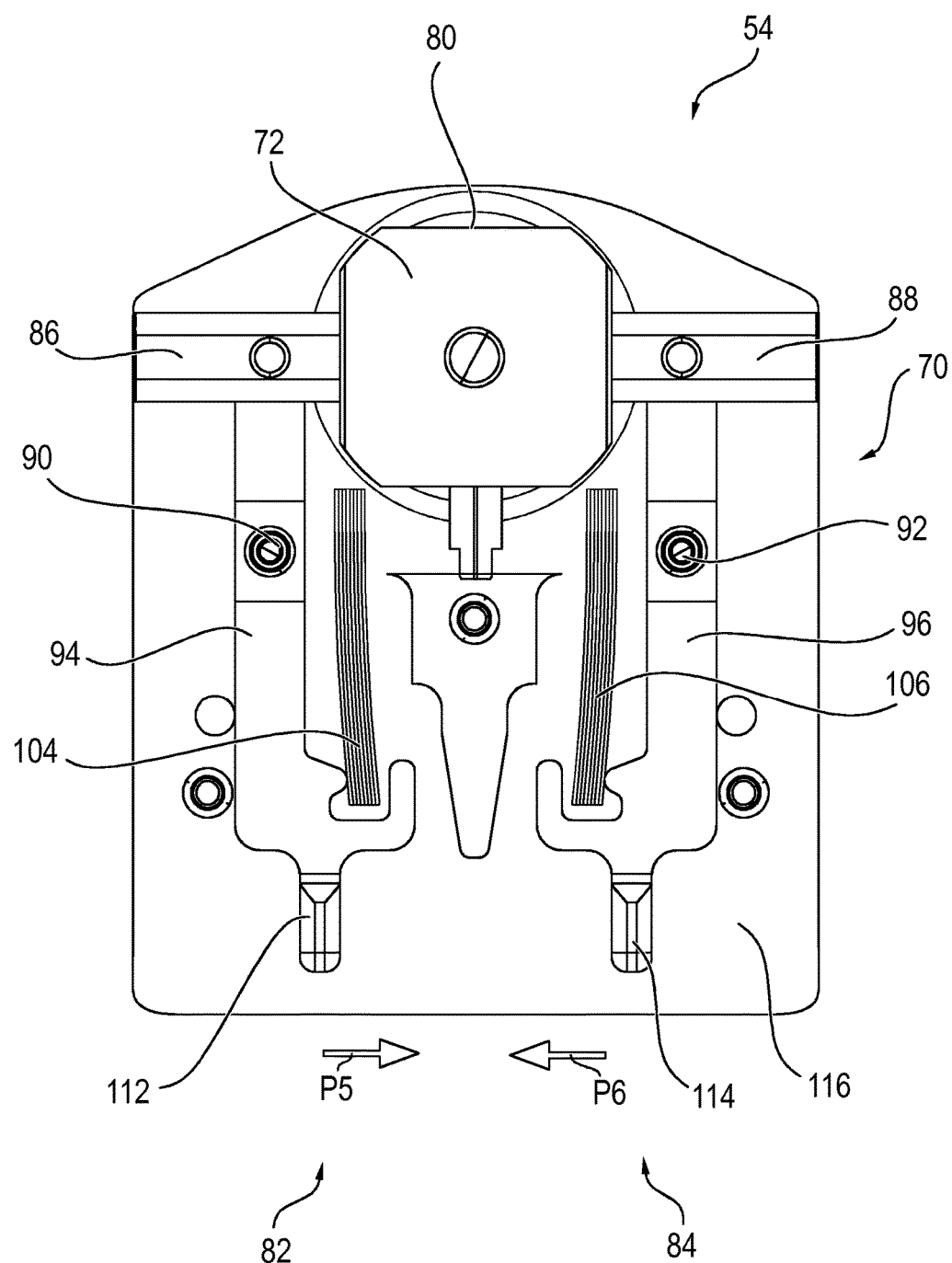
FIG. 7 shows a top view of a portion of the exemplary patient-supporting unit according to FIGS. 4 to 6.

In FIGS. 5 and 6, for example, a diagrammatic perspective representation of the height-adjustment unit 54 is shown, wherein a portion of the housing 66 may be cut out (e.g., so that the interior components of the locking unit 70 may be visible). In FIG. 7, a top view of the height adjustment unit 54 may be shown, wherein, for the visibility of the elements of the locking unit 70, the housing 66 and/or the resting pad 50 (e.g., the entire resting pad 50) may be cut out.

The locking unit 70 may comprise two locking mechanisms 82, 84 that may operate separately from one another. The locking mechanisms 82, 84 may be configured to be identical in construction, for example in an arrangement mirrored about a central axis of the locking unit 70.

Each locking mechanism 82, 84 may comprise a locking member such as, for example, a locking bar 86, 88, which may have a recess in which a lever 94, 96 (e.g., that may be rotatably mounted about a rotation axis 90, 92) may engage. A plurality of snap-in recesses 98, 100 may be formed on the rod 72, for example on two opposite sides. The snap-in recesses may be shaped to be complementary to the locking bars 86, 88.

In a locked position, the locking bars 86, 88 may each engage in one of the snap-in recesses 98, 100, so that the rod 72 may be held in the position predetermined thereby. Depending on which of the snap-in recesses 98, 100 the locking bars 86, 88 may be snapped in, a different distance between the resting pad 50 and the fastening unit 52 may result. For example, the height of the resting pad 52 relative to the rails 12, 14 may be settable.

Each locking mechanism 82, 84 may comprise a resilient member or element such as, for example, flexion spring 104, 106 by which the locking bars 86, 88 may be preloaded in the locked position. Via the levers 94, 96, the locking bars 86, 88 can be moved from the locked position into an unlocked position, against the resetting force of the flexion springs 104, 106 (for example, as illustrated by the arrows P1 and P2). If the levers 94, 96 are released, then the locking bars 86, 88 may be moved automatically back into the locked position by the resetting force of the corresponding springs 104, 106.

The snap-in recesses 98, 100 may have a beveled edge 108 and a non-beveled edge 110. By the beveled edge 108, the rod 72 can be moved upward (e.g., in the direction of the arrow P3), for example even if the locking bars 86, 88 are disposed (e.g., arranged) in the locked position. Also for example, when the rod 72 is moved upward, the locking bars 86, 88 may be automatically moved by the beveled edges 108 into the unlocked position, without an actuation of the lever 94, 96.

The non-beveled edges 110 may substantially prevent the rod 72 from being moved downward (e.g., in a substantially vertical direction such as, for example, in the direction of the arrow P4), for example, unless the two locking bars 86, 88 are disposed (e.g., arranged) in the unlocked position (e.g., in which they do not engage in any of the snap-in recesses 98, 100).

For example, to increase the distance of the resting pad 50 from the fastening unit 52, the resting pad 50 and the rod 72 may be pulled upward. Also for example, due to the double locking using the two locking mechanisms 82, 84, a movement (e.g., an inadvertent moving) of the resting pad 50 downward may also be prevented. Accordingly, in at least some exemplary embodiments, the patient may remain at the set height (e.g., a predetermined height) during the operation.

The end portions or end areas 112, 114 of the levers 94, 96, which may be actuated for the unlocking, may be arranged (e.g., inside a recess 116 of the housing 66) so that an actuation (e.g., an unintentional actuation) of the levers 94, 96 may be substantially prevented. Also for example, the likelihood of an actuation (e.g., an unintentional actuation) of the two levers 94, 96 may be reduced or substantially prevented because the two foot areas 112, 114 of the levers 94, 96 are moved in opposite directions for the unlocking of the respective locking bars 86, 88. For example, for the unlocking, the end area 112 of the lever 94 is moved in the direction P5, and the end area 114 of the lever 96 is moved in the direction P6 (e.g., they may be moved towards one another). For example, when moving from the locked position to the unlocked position, the first locking member (e.g., first locking bar 86) and the second locking member (e.g., second locking bar 88) move in opposite directions.

In at least some exemplary embodiments, because the two locking mechanisms 82, 84 may be configured so that they alone can bear a desired or predetermined weight (e.g., a maximum admissible weight), a movement of the rod 72 downward (e.g., in the direction of the arrow P4) may occur if the two locking mechanisms 82, 84 have been unlocked. Thus, the height adjustment unit 54 may operate suitably (e.g., in a consistent manner). For example, the locking assembly (e.g., locking unit 70) may be stationary relative to the fastening assembly (e.g., fastening unit 52), wherein the elongated member (e.g., rod 72) may be slidingly guided in an aperture (e.g., aperture 80) of the locking assembly (e.g., locking unit 70) in a longitudinal direction of the elongated member (e.g., rod 72). Also for example, a plurality of first snap-in recesses 98 may be disposed on a first side portion of the elongated member (e.g., rod 72), wherein the locking assembly (e.g., locking unit 70) may include a first locking member (e.g., first locking bar 86) and wherein the first locking member (e.g., first locking bar 86), in a locked position, may selectively engage in one of the plurality of first snap-in recesses 98 and may substantially prevent a movement of the elongated member (e.g., rod 72) in a first direction.

For example, on the rod 72, a groove 118 may be provided, in which a pin 120 may engages. The pin may be arranged, e.g. fixed relative to the fastening unit 52, on the fastening unit 52. Via the pin 120 being guided in the groove 118, a twisting of the rod 72 may be substantially prevented and the setting range within which the height can be adjusted (e.g., the setting range within which the distance between resting pad 50 and fastening unit 52 can be varied) may remain within a desired range.

For example, at the opposite end or end portion of the groove 118 from the resting pad 50, a resilient abutment 122 may be provided in the groove 118, by which the abutment behavior of the pin 120 at the groove end is damped and a tolerance compensation may be provided.

In at least some exemplary embodiments, the height adjustment unit 54 may be configured so that the distance between the resting pad 50 and the fastening unit 52 may be adjusted by 8 cm (e.g., within five steps or recesses). Also for example, the height adjustment can also have a relatively larger or smaller adjustment range. Also for example, any suitable number of steps or recesses, for example 4 or 6 steps, can be provided. Accordingly, any suitable number of snap-in recesses 98, 100 may be provided. Also, for example, a plurality of second snap-in recesses 100 may be disposed on a second side portion of the elongated member (e.g., rod 72), and the locking assembly (e.g., locking unit) may include a second locking member (e.g., second locking bar 88). Further, for example, in a locked position, the second locking member (e.g., second locking bar 88) may selectively engage in one of the plurality of second snap-in recesses 100 and may substantially prevent a movement of the elongated member (e.g., rod 72) in a first direction (e.g., P4).

In at least some exemplary embodiments of the invention, it a single locking mechanism 82, 84 may be provided (e.g., one locking mechanism). Also for example, two locking mechanisms 82, 84 can also be provided (for example, the two locking mechanisms may be actuated via a common lever).

The individual components of the patient-supporting unit 40 may be formed, for example, from a carbon-fiber-reinforced plastic or from any other suitable material (e.g., stable and/or x-ray permeable material). For example, the patient-supporting unit 40 may be constructed without metal. For example, a suitable x-ray image (e.g., a qualitatively high-value x-ray image) may be taken of a patient supported on the patient-supporting unit 40 to 46 (e.g., also in the area where the patient lies on the resting pad 50).

Figure 8:
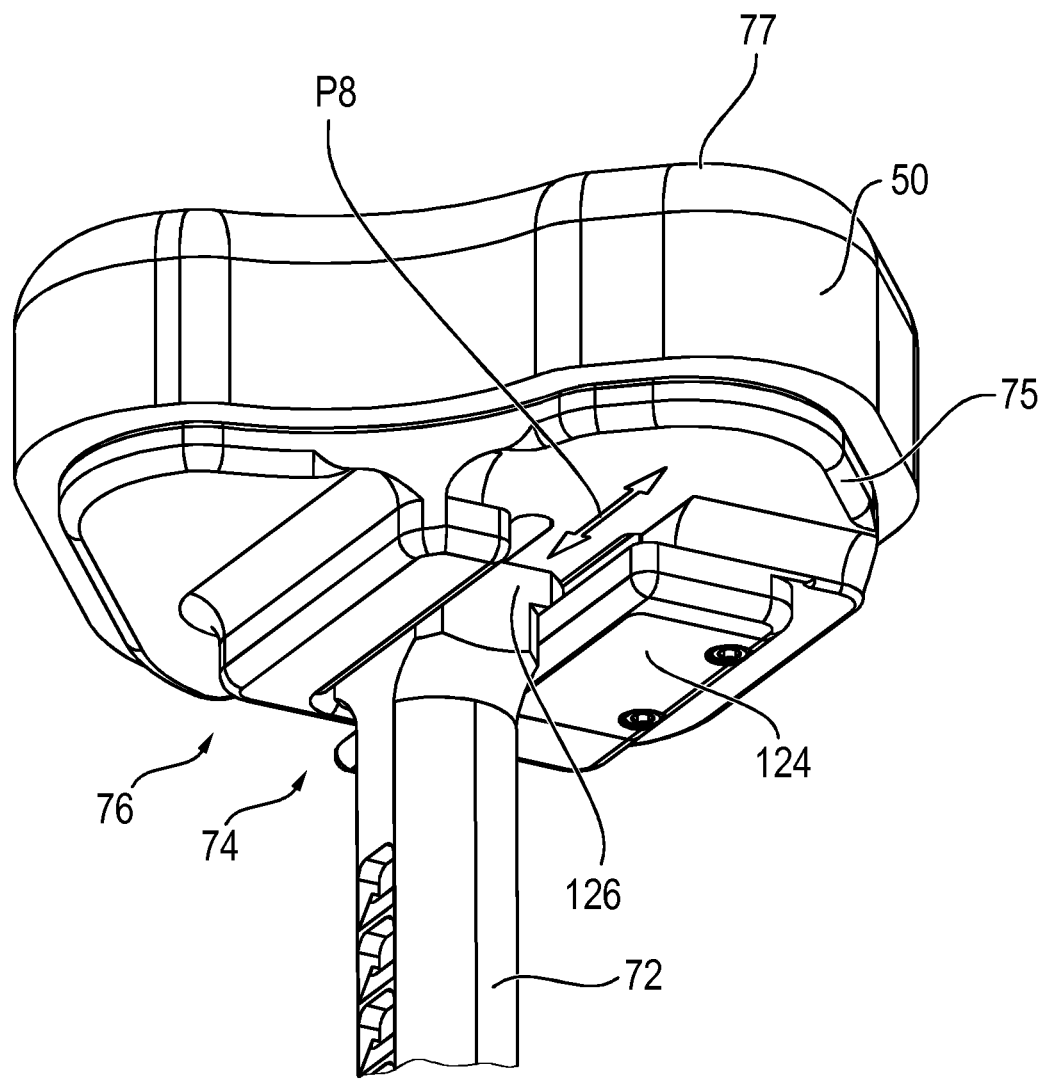
FIG. 8 shows another detail of the exemplary patient-supporting unit according to FIGS. 4 to 7.
Figure 9:
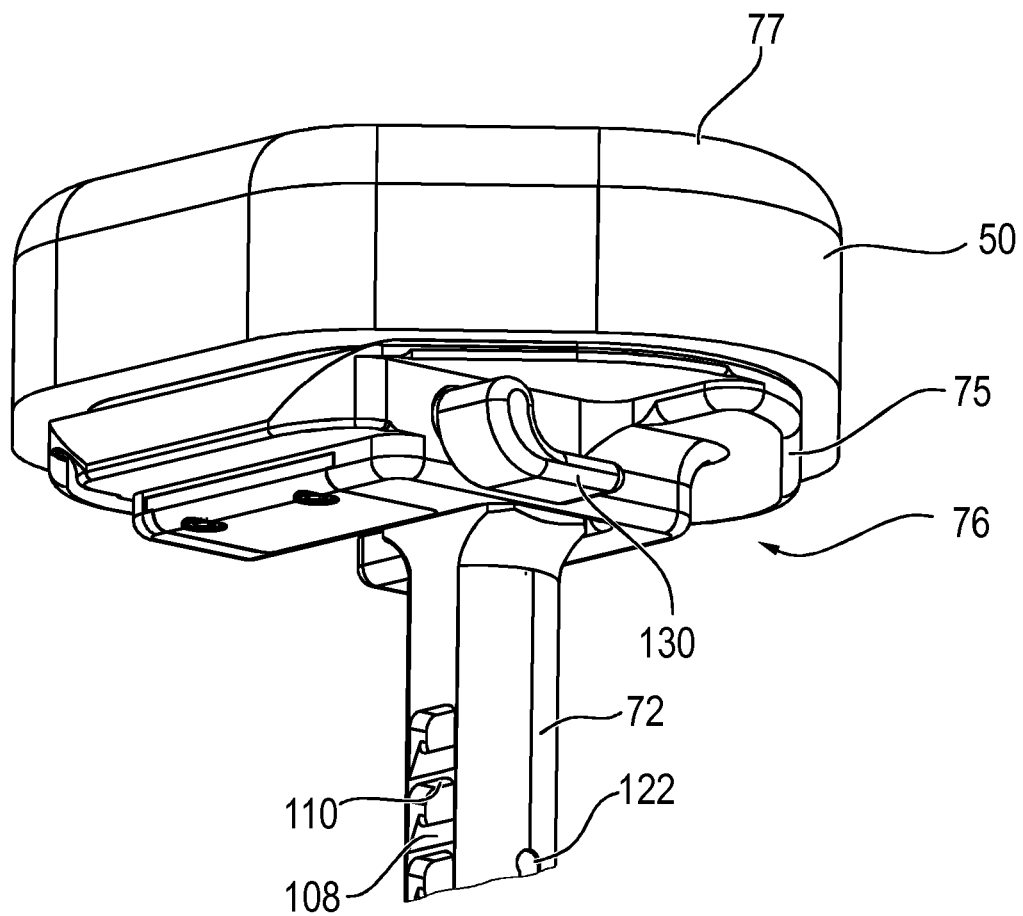
FIG. 9 shows another detail of the exemplary patient-supporting unit according to FIGS. 4 to 8.
Figure 10:
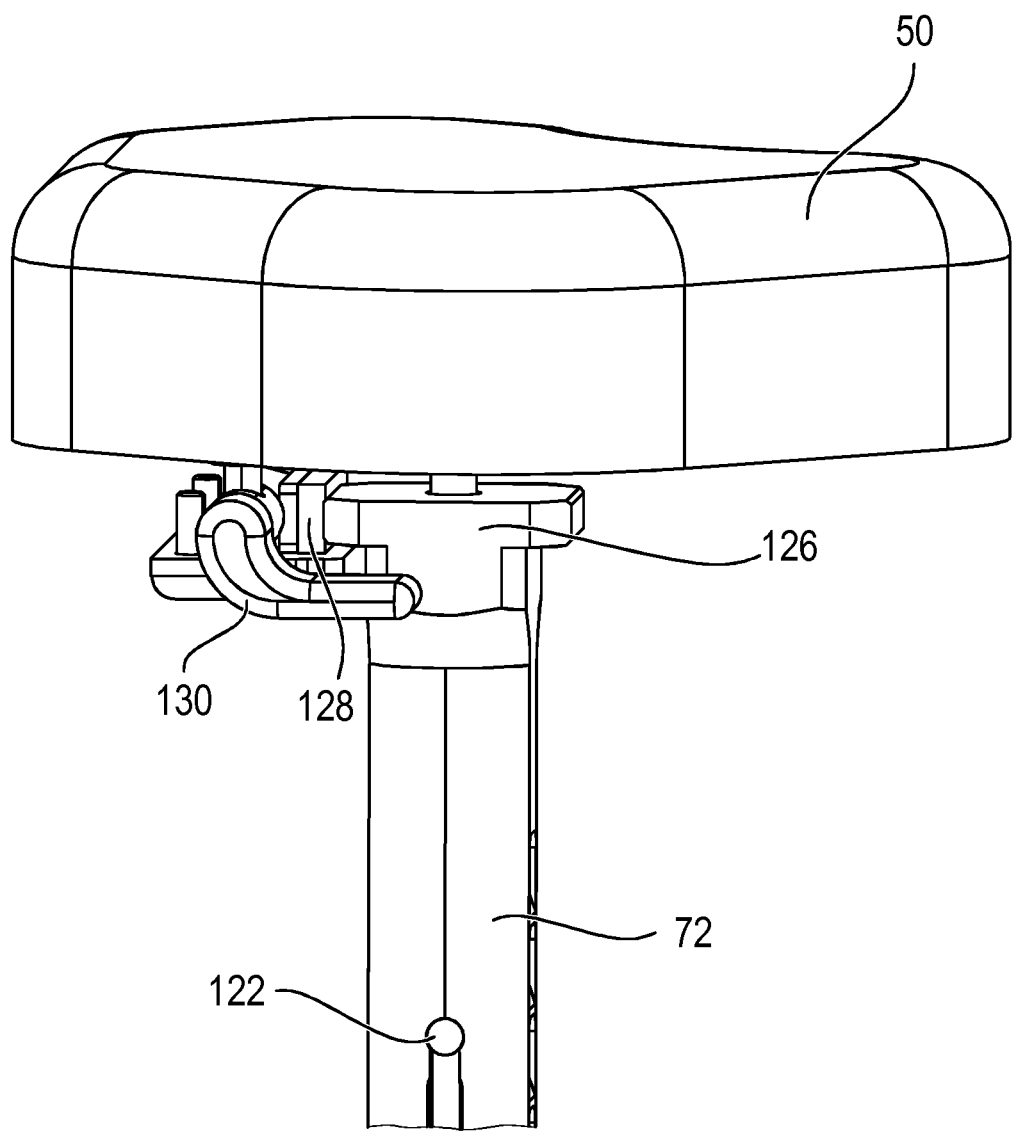
FIG. 10 shows another detail of the exemplary patient-supporting unit according to FIGS. 4 to 9.

In FIGS. 8 to 10, a diagrammatic perspective representation of a detail of the patient-supporting unit 40 according to FIGS. 4 to 7 is represented, wherein, for example, the cross adjustment assembly or unit 76 is depicted (e.g., by which the resting pad 50 can be adjusted relative to the rod 72 in a direction of the double arrow P8). For example, on the resting pad 50, a rail 124 may be arranged, into which a complementarily shaped head area 126 of the first end 74 of the rod 72 may protrude. The rail 124 may form, for example, a single part with the supporting structure 75.

Via a clamping lever 130, as represented in FIG. 10, in which the rail 124 may be cut out, clamping jaws 128 can be pressed against the head area 126 (e.g., so that, in the case in which the clamping lever 130 is tightened, a sliding of the resting pad 50 relative to the rod 72 may be reduced or substantially prevented). Also for example, if the clamping lever 130 is released, then the contact pressure of the clamping jaws 128 against the head area 126 of the rod 72 may also be released (e.g., so that the resting pad 50 may be slid in direction of the double arrow P8).

By this cross adjustment unit 76, the distance between the resting pads 50 of two adjacent patient-supporting units 40, 42 and 44, 46 arranged on different rails 12, 14 may be varied. For example, the free space between the resting pads 50 of these adjacent patient-supporting units 40, 42 and 44, 46 can be varied (e.g., so that the size of a free x-raying range in which substantially no material is arranged can be varied).

The direction P8, for example, may be oriented orthogonally with respect to the directions P3 and P4 in which the rod 72 is movable. Similarly for example, the adjustment direction P3, P4 of the rod 72 and the adjustment direction P8 of the cross adjustment unit 76 may be directed substantially orthogonally to the longitudinal axis of the rails 12, 14, (e.g., resulting in an adjustment of the resting pads 50 in all three directions) and the support of the patient can be suitably adapted to the individual anatomy of a patient.

It will be apparent to those skilled in the girt that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. A patient-supporting device, comprising:
   a fastening assembly that fastens the patient-supporting device to a structural member;
   a support member configured to receive a body part of a patient; and
   a height adjustment assembly that adjusts a distance between the fastening assembly and the support member;
   wherein the height adjustment assembly includes a locking assembly and an elongated member;
   wherein the support member is attached to a first end portion of the elongated member;
   wherein the locking assembly is stationary relative to the fastening assembly;
   wherein the elongated member is guided in an aperture of the locking assembly in a longitudinal direction of the elongated member;
   wherein a plurality of first snap-in recesses is disposed on a first side portion of the elongated member, and a plurality of second snap-in recesses is disposed on a second side portion of the elongated member;
   wherein the locking assembly includes a first locking member and a second locking member;
   wherein the first locking member, in a locked position, selectively engages in one of the plurality of first snap-in recesses and substantially prevents a movement of the elongated member in a first direction; and
   wherein in a locked position, the second locking member selectively engages in one of the plurality of second snap-in recesses and substantially prevents a movement of the elongated member in the first direction.

2. The patient-supporting device of claim 1, wherein the height adjustment assembly adjusts the distance between the fastening assembly and the support member by at least 5 cm.

3. The patient-supporting device of claim 1, wherein the height adjustment assembly adjusts the distance between the fastening assembly and the support member within a predetermined setting range, with the distance being set stepwise within the setting range.

4. The patient-supporting device of claim 1, wherein the plurality of first snap-in recesses, when viewed in the first direction, are beveled so that the elongated member can be moved in a second direction that is opposite the first direction when the first locking member is disposed in the locked position.

5. The patient-supporting device of claim 1, wherein:
the first locking member is movable between the locked position and an unlocked position; and
in the unlocked position, the first locking member allows a movement of the elongated member in the first direction.

6. The patient-supporting device of claim 5, wherein:
the first locking member is preloaded in the locked position by a resilient member; and
a first lever moves the first locking member against a resetting force of the resilient member, from the locked position into the unlocked position.

7. The patient-supporting device of claim 5, wherein the elongated member is movable in the first direction when the first locking member and a second locking member are disposed in the unlocked position.

8. The patient-supporting device of claim 1, wherein the plurality of second snap-in recesses, when viewed in the first direction, are beveled so that the elongated member is movable in the second direction when the second locking member is disposed in the locked position.

9. The patient-supporting device of claim 1, wherein:
the second locking member is movable between the locked position and an unlocked position; and
in the unlocked position, the second locking member moves the elongated member in the first direction.

10. The patient-supporting device of claim 9, wherein:
the second locking member is preloaded in the locked position by a resilient member; and
a second lever moves the second locking member against a resetting force of the resilient member, from the locked position into the unlocked position.

11. The patient-supporting device of claim 10, wherein the locking assembly is configured so that, for unlocking, the first lever and the second lever are moved in opposite directions.

12. The patient-supporting device of claim 10, wherein an end portion of the first lever and an end portion of the second lever are disposed in a recess of the fastening assembly.

13. A patient-supporting arrangement, comprising:
two rails, and at least one fastening unit configured for fastening the two rails to an operating table; and
a plurality of patient-supporting devices according to claim 1;
wherein the plurality of patient-supporting devices are each fastenable to said two rails via their respective fastening assemblies, such that the respective support members of the plurality of patient-supporting devices are oriented generally upwards, for supporting a patient thereon.

14. A patient-supporting device, comprising:
a fastening assembly that fastens the patient-supporting device to a structural member;
a support member configured to receive a body part of a patient; and
a height adjustment assembly that includes a locking assembly and an elongated member;
wherein the support member is attached to a first end portion of the elongated member;
wherein the elongated member is guided in an aperture of the locking assembly in a longitudinal direction of the elongated member;
wherein a plurality of snap-in recesses is disposed on a side portion of the elongated member;
wherein the locking assembly includes a locking member;
wherein the locking member, in a locked position, selectively engages in one of the plurality of snap-in recesses and substantially prevents a movement of the elongated member in a first direction;
wherein the locking member is preloaded in the locked position by a resilient member;
wherein a lever moves the locking member against a resetting force of the resilient member, from the locked position into the unlocked position;
wherein a groove is provided in the elongated member, a pin being connected to the fastening assembly protruding into the groove; and
wherein a resilient abutment is disposed at an end portion of the groove.

15. The patient-supporting device of claim 14, wherein at least one of the support member, the height adjustment assembly and the fastening assembly are formed from carbon fiber-reinforced plastic.

16. The patient-supporting device of claim 14, wherein the fastening assembly includes a U-shaped recess that receives the structural member and a plate that closes the U-shaped recess.

17. A patient-supporting device, comprising:
a fastening assembly that fastens the patient-supporting device to a structural member;
a support member configured to receive a body part of a patient; and
a height adjustment assembly that includes a locking assembly and an elongated member;
wherein the support member is attached to a first end portion of the elongated member;
wherein the elongated member is guided in an aperture of the locking assembly in a longitudinal direction of the elongated member;
wherein a plurality of snap-in recesses is disposed on a side portion of the elongated member;
wherein the locking assembly includes a first locking member and a second locking member;
wherein each of the first locking member and the second locking member, in a locked position, selectively engages in one of the plurality of snap-in recesses and substantially prevents a movement of the elongated member in a first direction;
wherein each of the first locking member and the second locking member is movable between the locked position and an unlocked position; and
wherein when moving from the locked position to the unlocked position, the first locking member and the second locking member move in opposite directions.

18. The patient-supporting device of claim 17, wherein a cross adjustment assembly moves the support member in a predetermined cross adjustment range relative to the height adjustment assembly.

19. The patient-supporting device of claim 18, wherein adjustment directions of the height adjustment assembly and the cross adjustment assembly are oriented substantially orthogonally with respect to each other.

20. A patient-supporting device, comprising:
a fastening assembly that fastens the patient-supporting device to a structural member;
a support member configured to receive a body part of a patient; and
a height adjustment assembly that includes a locking assembly and an elongated member;
wherein the support member is attached to a first end portion of the elongated member;

wherein the elongated member is guided in an aperture of the locking assembly in a longitudinal direction of the elongated member;

wherein a plurality of snap-in recesses is disposed on a side portion of the elongated member;

wherein the locking assembly includes a locking member;

wherein the locking member, in a locked position, selectively engages in one of the plurality of snap-in recesses and substantially prevents a movement of the elongated member in a first direction;

wherein the locking member is preloaded in the locked position by a resilient member;

wherein a lever moves the locking member against a resetting force of the resilient member, from the locked position into the unlocked position;

wherein the fastening assembly includes: a U-shaped recess that receives the structural member, and a plate that closes the U-shaped recess.

21. A patient-supporting arrangement, comprising:

two rails, and at least one fastening unit configured for fastening the two rails to an operating table; and a plurality of patient-supporting devices according to claim 20;

wherein the respective U-shaped recesses of the plurality of patient-supporting devices are shaped to receive, and lockable onto, said two rails.

* * * * *